US00PP29157P2

(12) United States Plant Patent
Bullis

(10) Patent No.: US PP29,157 P2
(45) Date of Patent: Mar. 27, 2018

(54) ***NEOREGELIA* PLANT NAMED 'KEY LARGO'**

(50) Latin Name: *Neoregelia carolinae×(Neoregelia meyendorfii×Neoregelia macrosepala)*
Varietal Denomination: Key Largo

(71) Applicant: Patricia E. Gomez Bullis, Princeton, FL (US)

(72) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 0 days.

(21) Appl. No.: 15/530,275

(22) Filed: Dec. 16, 2016

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — Annette H Para
(74) *Attorney, Agent, or Firm* — C. A. Whealy

(57) ABSTRACT

A new and distinct cultivar of *Neoregelia* plant named 'Key Largo', characterized by its broad and outwardly spreading growth habit; leaves that are close to horizontal in aspect; leaves that are dark green in color with distinct light yellow green-colored stripes and margins; when flowering, upper leaves are red purple in color; good interiorscape and landscape performance; and relative resistance to pathogens common to *Neoregelia* plants.

2 Drawing Sheets

Botanical designation: *Neoregelia carolinae*×(*Neoregelia meyendorfii*×*Neoregelia macrosepala*).

Cultivar denomination: 'KEY LARGO'.

BACKGROUND OF THE INVENTION

The present invention relates to a new and distinct cultivar of *Neoregelia* plant, botanically known as *Neoregelia carolinae*×(*Neoregelia meyendorfii*×*Neoregelia macrosepala*), and hereinafter referred to by the name 'Key Largo'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2006 in Princeton, Fla. of an unnamed proprietary selection of *Neoregelia carolinae*, not patented, as the female, or seed, parent with an unnamed proprietary selection of *Neoregelia meyendorfii*×*Neoregelia macrosepala*, not patented, as the male, or pollen, parent. The new *Neoregelia* plant was discovered and selected by the Inventor as a single plant within the progeny of the stated cross-pollination in a controlled greenhouse environment in Princeton, Fla. in 2006.

Asexual reproduction of the new *Neoregelia* plant by offsets in a controlled environment in Princeton, Fla. since 2007, has shown that the unique features of this new *Neoregelia* plant are stable and reproduced true to type in successive generations.

SUMMARY OF THE INVENTION

Plants of the new *Neoregelia* have not been observed under all possible combinations of environmental conditions and cultural practices. The phenotype may vary somewhat with variations in environment conditions such as temperature and light intensity without, however, any variance in genotype.

The following traits have been repeatedly observed and are determined to be the unique characteristics of 'Key Largo'. These characteristics in combination distinguish 'Key Largo' as a new and distinct *Neoregelia* plant:

1. Broad and outwardly spreading growth habit.
2. Leaves that are close to horizontal in aspect.
3. Leaves that are dark green in color with distinct light yellow green-colored stripes and margins; when flowering, upper leaves are red purple in color.
4. Good interiorscape and landscape performance.
5. Relatively resistant to pathogens common to *Neoregelia* plants.

Plants of the new *Neoregelia* differ primarily from plants of the female parent selection in the following characteristics:

1. Plants of the new *Neoregelia* are broader than plants of the female parent selection.
2. Leaves of plants of the new *Neoregelia* are more horizontal than and not as arching as leaves of plants of the female parent selection.
3. Plants of the new *Neoregelia* and the female parent selection differ in leaf color as plants of the female parent selection are variegated.
4. Flowering plants of the new *Neoregelia* and the female parent selection differ in upper leaf color as flowering plants of the female parent selection have orange-colored upper leaves.

Plants of the new *Neoregelia* differ primarily from plants of the male parent selection in the following characteristics:

1. Plants of the new *Neoregelia* and the male parent selection differ in leaf color as plants of the male parent selection have green-colored leaves that are tinged with red.

2. Flowering plants of the new *Neoregelia* and the male parent selection differ in upper leaf color as flowering plants of the male parent selection have red-colored upper leaves.

Plants of the new *Neoregelia* can be compared to plants of the *Neoregelia carolinae* 'Flandria', not patented. In side-by-side comparisons conducted in Princeton, Fla., plants of the new *Neoregelia* and 'Flandria' differed primarily in the following characteristics:

1. Plants of the new *Neoregelia* are broader than plants of 'Flandria'.
2. Leaves of plants of the new *Neoregelia* are more horizontal than and not as arching as leaves of plants of 'Flandria'.
3. Leaf coloration pattern of plants of the new *Neoregelia* is more stable than leaf coloration pattern of plants of 'Flandria'.
4. Flowering plants of the new *Neoregelia* and 'Flandria' differ in upper leaf color as flowering plants of 'Flandria' have red orange-colored upper leaves.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph on the first sheet is a top perspective view of a typical flowering plant of 'Key Largo' grown in a container.

The photograph on the second sheet is a close-up view of a typical flowering plant of 'Key Largo'.

DETAILED BOTANICAL DESCRIPTION

The aforementioned photographs and following observations, measurements and values describe flowering plants grown during the summer and autumn in 15-cm containers in a polypropylene-covered greenhouse in Princeton, Fla. and under cultural practices typical of commercial *Neoregelia* production. During the production of the plants, day temperatures ranged from 18° C. to 30° C., night temperatures ranged from 18° C. to 28° C. and light levels ranged from 2,500 to 3,200 foot-candles. Plants were twelve months old when the photographs and description were taken. In the following description, color references are made to The Royal Horticultural Society Colour Chart, 2007 Edition, except where general terms of ordinary dictionary significance are used.

Botanical classification: *Neoregelia carolinae*×(*Neoregelia meyendorfii*×*Neoregelia macrosepala*) 'Key Largo'.

Parentage:

*Female, or seed, parent*.—Unnamed proprietary selection of *Neoregelia carolinae*, not patented.

*Male, or pollen, parent*.—Unnamed proprietary selection of *Neoregelia meyendorfii*×*Neoregelia macrosepala*, not patented.

Propagation:

*Type*.—By offsets.

*Time to initiate roots, summer*.—About 30 to 45 days at ambient temperatures about 28° C. to 30° C.

*Time to initiate roots, winter*.—About 45 to 60 days at ambient temperatures about 28° C. to 30° C.

*Time to produce a rooted young plant, summer*.—About three months at ambient temperatures about 28° C. to 30° C.

*Time to produce a rooted young plant, winter*.—About four months at ambient temperatures about 18° C. to 22° C.

*Root description*.—Medium in thickness, fibrous; typically yellow to beige tan in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Broad and outwardly spreading growth habit; rosette leaves are erect when young, becoming close to horizontal in aspect with development; plants readily produce uniform offsets; vigorous growth habit.

*Plant height*.—About 16 cm.

*Plant diameter or spread*.—About 55 cm.

*Internode length*.—About 4 mm.

*Stem diameter at the soil level*.—About 3 cm.

*Stem texture*.—Smooth, glabrous.

*Stem color*.—Close to NN155A.

Leaf description:

*Arrangement*.—Rosette, spiral phyllotaxis; simple; sessile, clasping.

*Shape*.—Narrowly oblong with broad sheathing base.

*Apex*.—Cuspidate.

*Base*.—Truncate, clasping.

*Margin*.—Serrate, spinose.

*Length*.—About 33 cm.

*Width, mid-section*.—About 5.25 cm.

*Width, base*.—About 7.5 cm.

*Texture and luster, upper and lower surfaces*.—Smooth, glabrous; leathery; longitudinally ribbed; glossy, shiny.

*Venation pattern*.—Parallel.

*Color*.—Lower leaves, upper surface: Centers, close to 147A; towards the base, close to 148A to 148B; longitudinal stripes, close to 154D; margins, close to 8C tinged with close to 144A; venation, similar to lamina colors. Lower leaves, lower surface: Centers, close to 147A; towards the base, close to 146A; longitudinal stripes, close to 8D; margins, close to 8C tinged with close to 144A; venation, similar to lamina colors. Upper leaves, upper surface: Closest to N57A; towards the base, close to 160D; venation, similar to lamina colors. Upper leaves, lower surface: Closest to 54A; towards the base, close to 160D; venation, similar to lamina colors.

Inflorescence description:

*Inflorescence form*.—Terminal flat-topped compact corymb located inside the leaf rosette; about 96 flowers develop per inflorescence.

*Time to flower*.—Plants begin flowering about nine to eleven weeks after planting; plants flower naturally during the spring in Florida.

*Flower longevity*.—Individual flowers last about one to two days on the plant; flowers persistent; inflorescences last about eight weeks in the interiorscape and about 16 weeks in the landscape.

*Fragrance*.—None detected.

*Inflorescence length*.—About 6 cm.

*Inflorescence diameter*.—About 5.2 cm.

*Flower size*.—Length: About 5.2 cm. Diameter: About 7 mm.

*Flower buds*.—Length: About 3.3 cm. Diameter: About 5 mm. Shape: Narrowly elongate. Color: Close to 144A; towards the base, close to NN155D.

*Petals*.—Quantity per flower: Three in a single whorl. Shape: Oblanceolate. Apex: Sharply acuminate. Base: Truncate. Margin: Entire. Length: About 3.3 cm. Width: About 6 mm. Texture and luster, upper and lower surfaces: Smooth, glabrous; matte. Color: When opening, upper (inner) surface: Close to 93B; towards the base, close to NN155D. When opening, lower (outer) surface: Close to 93D; towards the base, close to NN155D. Fully opened, upper (inner) surface: Close to 93B, 93C and 93D; towards the base, close to NN155D. Fully opened, lower (outer) surface: Close to 93D; towards the base, close to NN155D.

*Flower bracts*.—Quantity per flower: One. Shape: Narrowly oblong. Length: About 3.5 cm. Width: About 7 mm. Texture, upper and lower surfaces: Membraneous. Color, upper and lower surfaces: Close to 145D.

*Sepals*.—Quantity per flower: Three in a single whorl. Shape: Narrowly oblong. Apex: Acuminate. Base: Truncate. Margin: Entire. Length: About 2.4 cm. Width: About 5 mm. Texture and luster, upper and lower surfaces: Smooth, glabrous; glossy, shiny. Color, upper surface: Close to 146C to 146D; towards the base, close to 145D. Color, lower surface: Close to 146C to 146D; towards the base, closer to 146D.

*Peduncles*.—Length: About 1.5 cm. Diameter: About 1.5 cm. Strength: Strong. Aspect: Typically erect. Texture: Smooth, glabrous. Color: Close to NN155D.

*Pedicels*.—Length: About 7 mm. Diameter: About 2.5 mm. Strength: Strong. Aspect: Typically erect to outward and curving upright. Texture: Smooth, glabrous. Color: Close to NN155D.

*Stamens*.—Quantity per flower: Six. Filament length: About 1 cm; partially adnate to the petals. Filament color: Close to NN155D. Anther shape: Lanceolate. Anther length: About 5 mm. Anther color: Close to 158C. Pollen amount: Scarce. Pollen color: Close to 158B to 158C.

*Pistils*.—Quantity per flower: One. Pistil length: About 2.75 cm. Stigma shape: Elongated oblong. Stigma color: Close to 157C. Style length: About 2 cm. Style color: Close to NN155D. Ovary color: Close to 155A to 155B.

*Fruits and seeds*.—To date, fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance.

Pathogen & pest resistance: Plants of the new *Neoregelia* have been observed to be relatively resistant to pathogens such as *Pythium, Phytophthora, Exserohilium* and *Fusarium*. Resistance to pests and other pathogens common to *Neoregelia* plants has not been observed.

It is claimed:

1. A new and distinct *Neoregelia* plant named 'Key Largo' as illustrated and described.

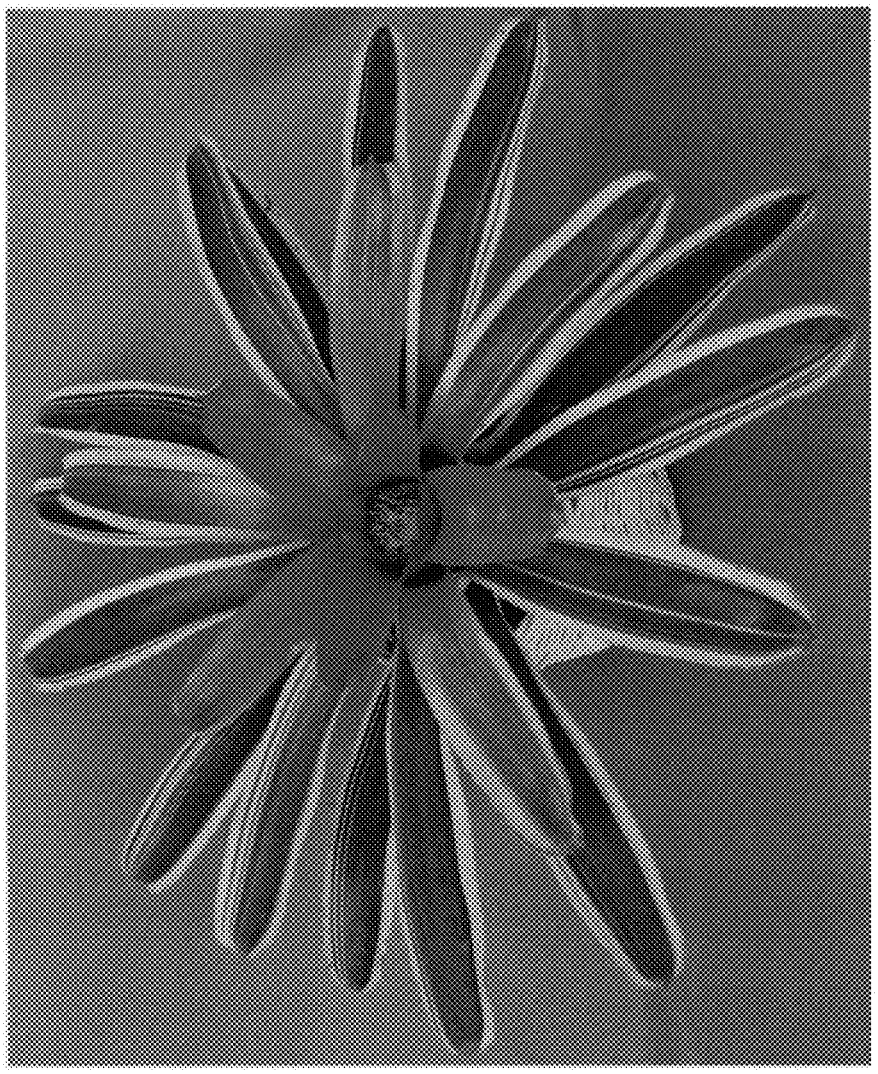

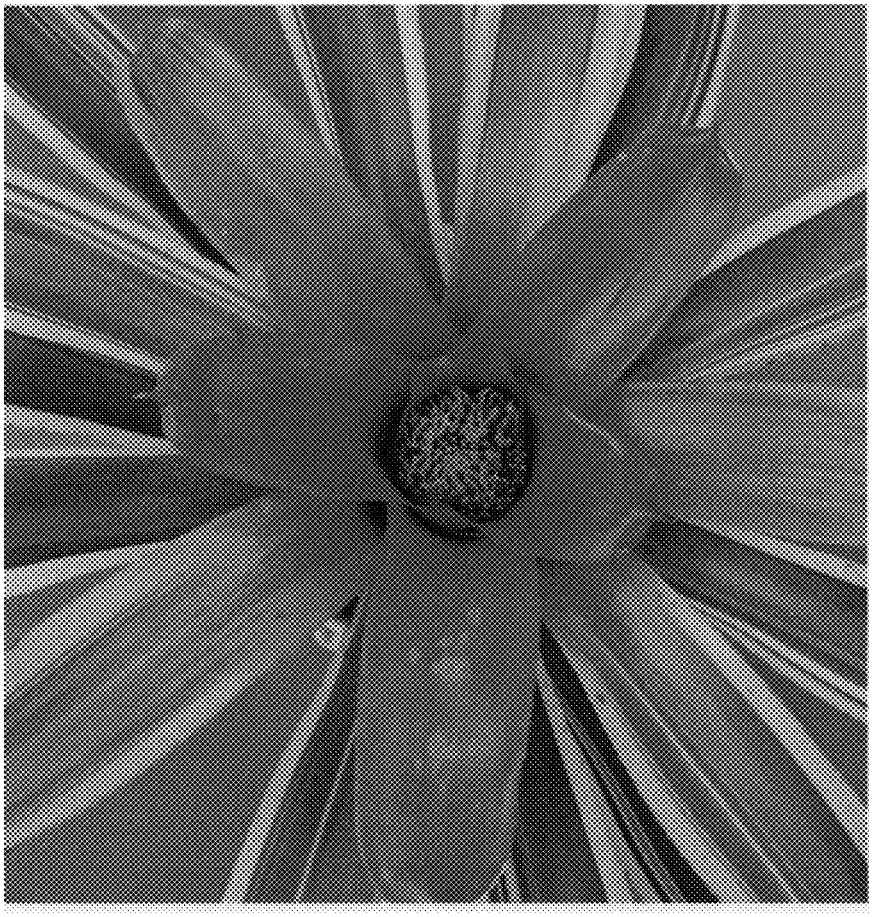

* * * * *